(12) United States Patent
Tissington et al.

(10) Patent No.: US 7,712,610 B2
(45) Date of Patent: May 11, 2010

(54) SENSOR VIAL HAVING A DEFORMABLE SEAL

(75) Inventors: Bryan Tissington, St. Neots (GB); Joanne Christine Slater, Nairn (GB)

(73) Assignee: Lifescan Scotland Limited, Inverness, Scotland (GB)

( * ) Notice: Subject to any disclaimer, the term of this patent is extended or adjusted under 35 U.S.C. 154(b) by 774 days.

(21) Appl. No.: 11/553,257

(22) Filed: Oct. 26, 2006

(65) Prior Publication Data

US 2008/0110894 A1    May 15, 2008

(51) Int. Cl.
*A61B 19/02* (2006.01)
*B65D 85/30* (2006.01)
*B65D 85/62* (2006.01)
*B65D 43/16* (2006.01)
*B65D 53/02* (2006.01)

(52) U.S. Cl. .................. 206/438; 206/456; 206/499; 220/283; 220/378; 220/849

(58) Field of Classification Search .............. 206/438, 206/499, 569, 449, 456; 220/281, 283, 326, 220/378, 834, 839, 803, 804, 809, 849; 277/637, 277/641, 642
See application file for complete search history.

(56) References Cited

U.S. PATENT DOCUMENTS

| | | | | |
|---|---|---|---|---|
| 2,723,142 A * | 11/1955 | Stebbins | ........................ | 220/803 |
| 2,910,209 A * | 10/1959 | Nelson | ........................ | 220/378 |
| 3,064,853 A * | 11/1962 | Lents et al. | ................... | 220/804 |
| 4,526,281 A | 7/1985 | Herr | | |
| 5,505,308 A | 4/1996 | Eikmeier et al. | | |
| 5,788,064 A * | 8/1998 | Sacherer et al. | .............. | 220/281 |
| 5,988,423 A * | 11/1999 | Auzureau | .................... | 220/378 |
| 6,050,199 A * | 4/2000 | Anderson et al. | ........... | 220/378 |
| 6,378,702 B1 * | 4/2002 | Kintzig | ........................ | 206/456 |
| 6,645,635 B2 | 11/2003 | Muraki | | |
| 6,769,558 B1 | 8/2004 | Bucholtz | | |
| 7,059,492 B2 * | 6/2006 | Giraud et al. | ................ | 220/839 |
| 2006/0006578 A1 * | 1/2006 | Johnson et al. | .............. | 264/242 |
| 2007/0034630 A1 * | 2/2007 | Lancesseur et al. | ......... | 220/281 |
| 2007/0080093 A1 * | 4/2007 | Boozer et al. | ................ | 206/569 |

FOREIGN PATENT DOCUMENTS

| | | |
|---|---|---|
| EP | 0 786 630 A1 | 7/1997 |
| EP | 0625948 | 4/2000 |
| GB | 788148 | 12/1957 |
| GB | 2222821 | 3/1990 |
| WO | WO 94/10558 A1 | 5/1994 |
| WO | WO 95/24301 | 9/1995 |
| WO | WO 03/042691 A1 | 5/2003 |
| WO | WO 2004/026695 A2 | 4/2004 |
| WO | WO 2006/000792 | 1/2006 |

* cited by examiner

*Primary Examiner*—Bryon P Gehman
(74) *Attorney, Agent, or Firm*—Lois Gianneschi

(57) ABSTRACT

The present invention is directed to a vial including a stack of test sensors, wherein the vial includes a vial body and a vial cap and a seal. In one embodiment of the present invention, the seal includes an annular ledge, a flange attached to the annular ledge, a hinge, also referred to as an annular line of weakness, and a skirt. In one embodiment of the present invention, the annular line of weakness is positioned between the skirt and the flange such that the skirt folds outward when pressure is applied to the annular ledge, such as, for example, when the skirt is pressed against a sealing surface of the vial body.

4 Claims, 11 Drawing Sheets

SENSOR VIAL HAVING A DEFORMABLE SEAL

FIELD OF THE INVENTION

The present invention relates to a seal for use in, for example, a vial used to store test sensors. More particularly, the present invention is directed to designs for such seals and to a method of manufacture of such a seal and a method of one of such a seal.

BACKGROUND TO THE INVENTION

Many modern industries and in particular the diabetes monitoring industry are presented with the challenge of providing a vial that provides isolation from environmental factors, convenience and easy opening of the vial and facilitates the extraction of a test sensor from a vial. Yet another challenge is the use of the test sensors by people with disabilities. Yet another challenge is providing a seal for a vial that can be used for automated dispensing of a test sensor from a vial.

The invention aims to alleviate at least some of the above-identified problems and/or needs. The present invention may optionally be used for a test sensor for testing for an analyte or indicator such as glucose concentration, HbAlc, cholesterol, etc in a bodily fluid such as urine, interstitial fluid (ISF), plasma or blood.

Patent application number GB2222821A describes 'Closures for Releasably Sealing Containers'. Patent application number. GB788148A describes 'Improvements in or Relating to Closures for Containers'. U.S. Pat. No. 4,526,281 describes a 'Moisture Tight Closure and Container'. Patent application number WO95/24301 describes a 'Partially Laminated Rubber Closure'. Patent number EP0625948B1 describes 'A Releasable Cap'.

SUMMARY OF THE INVENTION

The present invention is directed for a vial including a stack of test sensors, wherein the vial includes a vial body and a vial cap and a seal. In one embodiment of the present invention, the seal includes an annular ledge, a flange attached to the annular ledge, a hinge, also referred to as an annular line of weakness, and a skirt. In one embodiment of the present invention, the annular line of weakness is positioned between the skirt and the flange such that the skirt folds outward when pressure is applied to the annular ledge, such as, for example, when the skirt is pressed against a sealing surface of the vial body.

The present invention is further directed to a vial including a stack of test sensors, wherein the vial includes a vial body, a vial cap, the vial including a seal. In one embodiment of the invention, the seal includes a substantially planar upper wall, an annular mating face, an annular ledge connected to the annular mating face, an annular flange connected to the annular ledge, an annular hinge and a skirt. In this embodiment of the invention, the annular hinge is positioned between the annular flange and the skirt such that the skirt folds outward when pressure is applied to the skirt.

BRIEF DESCRIPTION OF THE DRAWINGS

A better understanding of the features and advantages of the present invention will be obtained by reference to the following detailed description that sets forth illustrative embodiments by way of example only, in which the principles of the invention are utilized, and the accompanying drawings of which.

DETAILED DESCRIPTION OF THE DRAWINGS

Figure 1:
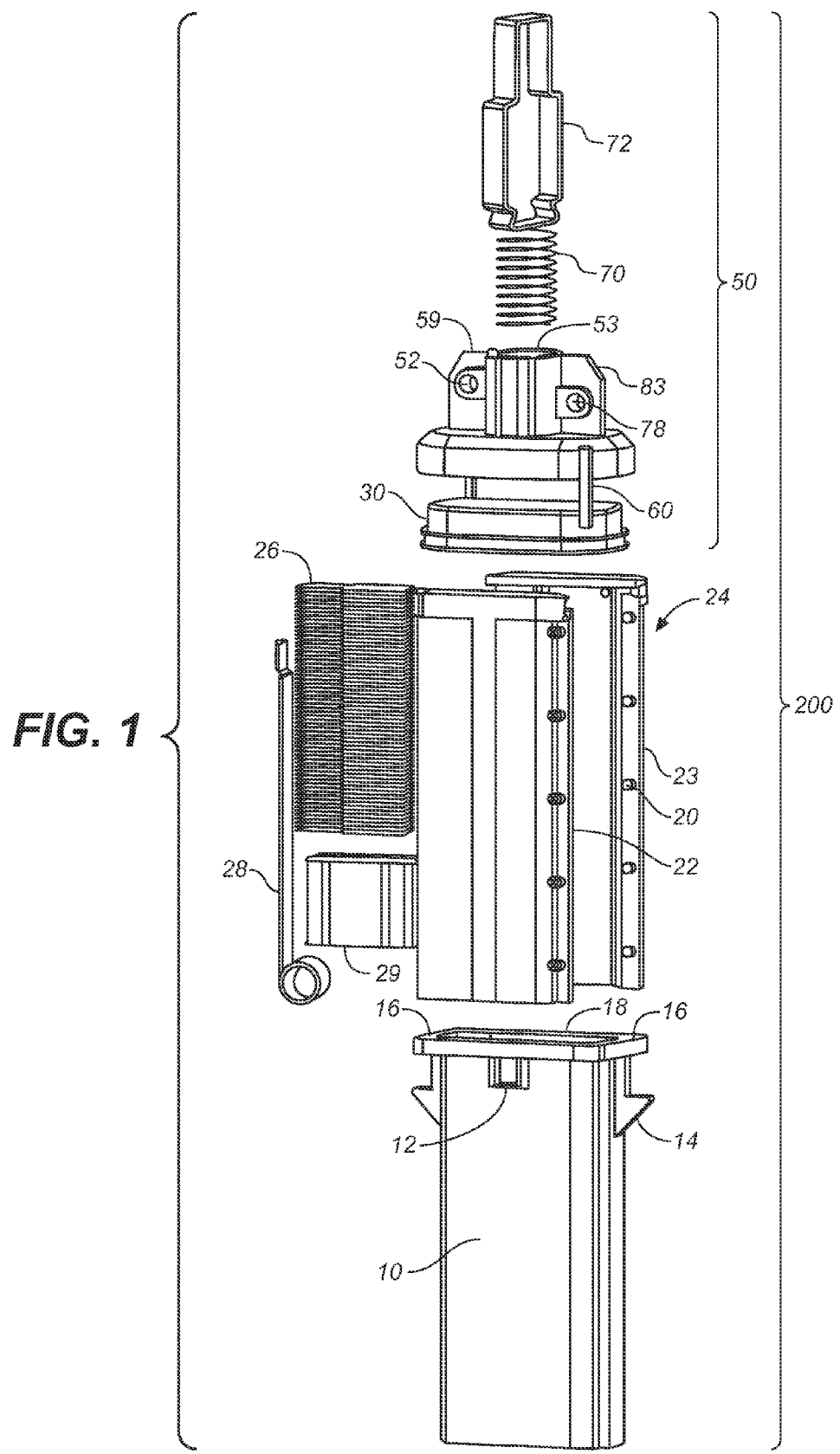
FIG. 1 shows an exploded view of a resealable vial according to an example embodiment of the invention.

FIG. 1 shows an exploded view of a vial 200 according to one example embodiment of the invention, comprising a vial body 10, a vial cap 50, U-shaped permanent clip 72, a coil spring 70, a rebate 53 with a cylinder-shaped inner surface, wings 59, 83 including offset holes 52, 78 respectively, location pins 60, a seal 30, an inner cassette 24 comprising two halves 22 and 23, protrusions 20, a stack of test sensors 26, a constant force spring 28, a loader 29, offset retention wings 14, rebates 12 for receiving U-shaped permanent clip 72, a sealing counter face 18 and apertures 16 for receiving location pins 60.

FIG. 1 shows an exploded perspective view of an embodiment of a vial 200 that may be used for housing a plurality of test sensors according to the present invention. Vial 200 is disposable and replaceable, and typically manufactured in two parts; a vial body 10, made in one piece from a high strength material such as polypropylene with 20% glass fibre reinforcement (available from Borealis, Denmark) with triangular shaped retention wings 14, that may or may not be offset with respect to each other, on each side panel which cooperate with corresponding rebates (not shown) within the meter; and a vial cap 50 that includes two holes 52, that also may or may not be offset with respect to each other, located in wing regions on either side of cap 50 which cooperate with a cap lifter (not shown). Holes 52 and/or wings 14 and rebates may be offset with the purposes of allowing the vial 200 to be inserted into a meter in one orientation only. Vial 200 may be black in colour or any other dark colour deemed to have sufficient properties to block light. Although this example embodiment utilizes round shaped holes, it would be obvious to a person skilled in the art that varying shapes and sizes of holes, including slots or other means to allow fixture of vial 200 to the cap lifter is conceivable, and is not restricted. Oval or teardrop shaped holes may facilitate replacement of vial 200 when required.

Retention features 14 could be triangular shaped protrusions, or other means of retaining vial body 10 rigidly within the meter to resist further upwards movement during actuation of the test sensor delivery mechanism.

A U-shaped clip 72 straddles cap 50, resting on top of a coil spring 70 located within a cylinder-shaped rebate 53. Clip 72 interlocks with vial body 10 at rebates 12 located directly under the sealing counter-face 18 of vial body 10. Clip 72 is made of steel or other suitably rigid material, and is permanently attached to vial 200 during manufacture and stays attached to vial 200 during use i.e. during opening and closing for test strip dispensing. A Santoprene™ (Advanced Elastomer Systems) rubber seal 30, or alternative suitably resiliently deformable material is two-shot moulded into, and lines the underside of vial cap 50. Rubber seal 30 also overlaps the periphery of the rim of vial cap 50 and deforms (approximately 0.4 mm) when a force (approximately 7N) is applied, thereby providing a substantially moisture semi-impermeable seal when depressed against counterface 18 on vial body 10.

Location pins 60 are provided on two diagonally opposite corners of cap 50, and cooperating rebates 16 are located on the corresponding corners of vial body 10 to receive location pins 60. An inner cassette 24 is housed within vial body 10 and is manufactured in two halves (items 22 and 23) that join at protrusions 20 and corresponding holes (not shown). Inner cassette 24 contains 10, 25, 50 or 100 test sensors, typically strips, usually arranged in a stack 26. A constant force spring 28 provides a force (around 1.5 N) on the underside of a loader 29 at the base of the stack of strips 26, thereby maintaining the test sensors in a position ready to be dispensed from with the vial 200.

While the term 'strip' is used herein to describe a test sensor typically used by patients to determine their blood glucose concentration, it would be apparent to a person skilled in the art that test sensors of shapes different from a strip can be envisaged from this disclosure.

A vial 200 of the type described in relation to FIG. 1 provides a robust means of storing a plurality of test sensors such as those used by patients to regularly determine their blood glucose concentration. It would be apparent to a person skilled in the art that a vial of the type described herein could be used to house test sensors used to measure the concentration of another analyte, indicator or body fluid.

The environmental conditions experienced by the test sensors within the vial 10 would typically be maintained at the correct specification to attain the expected lifetime and performance of the test sensors. These conditions typically exist inside vial 200 during both normal use within a blood glucose meter for example, and while vial 200 is retained for future use outside the meter, provided other storage instructions such as expiry date are followed. Vial 200 helps maintain the appropriate environmental conditions due to the closing action of clip 72. Exposure to inappropriate environmental conditions e.g. temperature or moisture, or to contamination from substances could potentially lead to the test sensors producing erroneous results.

Figure 2:
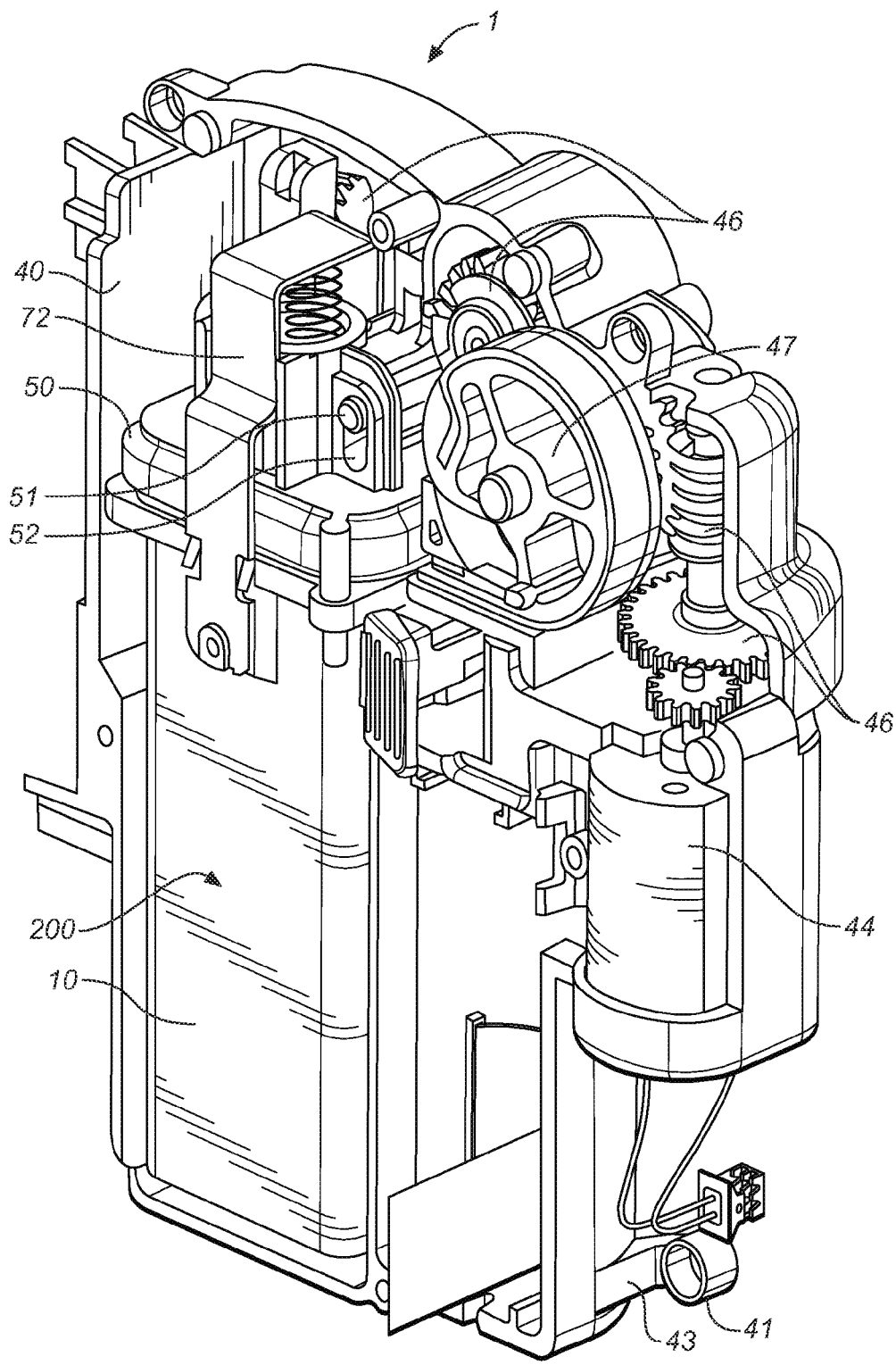
FIG. 2 shows a perspective view of an example embodiment of a blood glucose meter with main outer housing removed and a vial and feeding mechanism revealed.

FIG. 2 shows an example embodiment of a meter 1 incorporating a vial 200, comprising a mid frame 40, a gear train 46, a pusher wheel 47, a vial body 10, a vial cap 50 including a U-shaped permanent clip 72, holes 52, lifting pegs 51, a DC motor 44, a PCB 43 and a stereo jack 41.

FIG. 2 is a perspective view of an example embodiment of a blood glucose meter 1 for use with the present invention. Meter 1 is shown with its main outer housing removed to reveal vial 200 and a test sensor dispensing mechanism. Vial 200 is replaceable and accessible to the user through a door (not shown) optionally on the rear of meter 1. Vial 200 is held securely, within a cavity (not shown) provided specifically for receiving vial 200 in mid frame 40 by the cooperation of offset interlocking rebates (item 14 described in more detail in relation to FIG. 1) and also interaction between holes 52, 78 in vial cap 50 and lifting pins 51 (a component of the test sensor dispensing mechanism).

A stereo jack 41 is incorporated on PCB 43 to facilitate the transfer of measured data parameters stored within the meter memory to a Personal Computer (not shown) for further analysis. Analysis of measured parameters by a user, using software written specifically for this purpose, helps the user (and/or Health Care Practitioner) understand and better control the disease.

The internal test sensor delivery mechanism consists mainly of a gear train 46, which is described in detail in related patent application WO2006/000792A1, 'An automated motorized apparatus and method for dispensing test strips' filed Jun. 28, 2005 by LifeScan Scotland Ltd., the content of which is incorporated herein by reference. To dispense a test sensor, the user may press an actuation button (not shown) located on the outer housing of a dispensing meter. Such an actuation button operates motor 44, which in turn drives gear train 46 to deliver a test sensor to the user. This simple, one-stage user operation causes the internal test sensor delivery mechanism to perform two operations in sequence. The first action operates to open vial 200, whereby gearing mechanism 46 operates lifting pins 51 to disengage vial cap 50 from vial body 10. Locating pins 60 move out of apertures 16. The second action follows in sequence, whereby pusher wheel 47 turns and drives a test sensor pushing member to engage with the first test sensor presented by the stack, and deliver it to a test port (not shown). Following delivery of a test sensor to the test port, the polarity of motor 44 is reversed and the sequence of events occurs in reverse order to close vial 200 and maintain the moisture semi-impermeable seal. This sequence of events is discussed in related patent application WO2006/000792A1.

Figure 3:
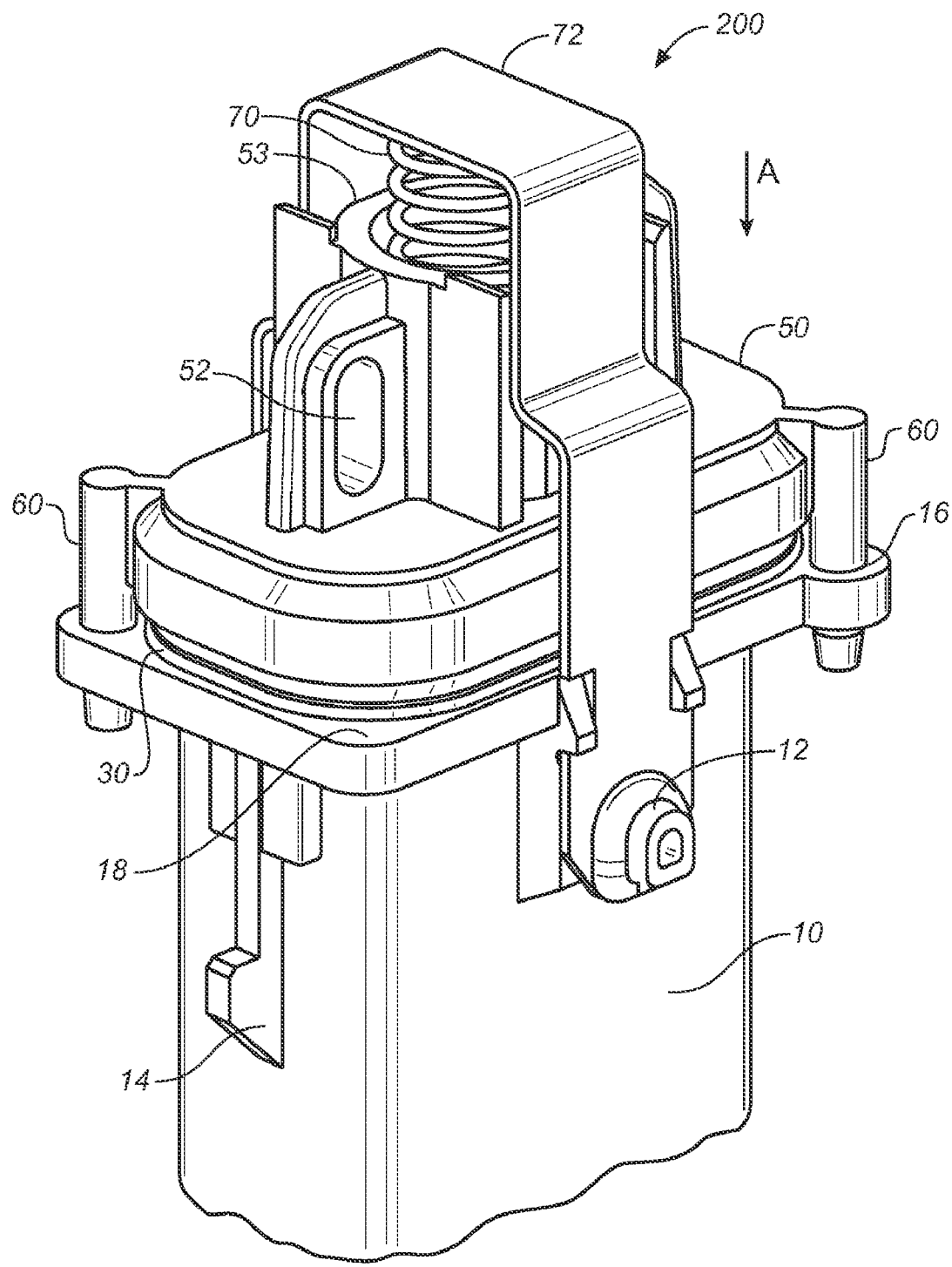
FIG. 3 shows a close up perspective view of an upper portion of the vial of FIGS. 1 and 2 shown in a closed position.

FIG. 3 shows a close up perspective view of vial 200 according to an example embodiment of the invention, comprising a vial body 10, a rebate 12, offset retention wings 14, apertures 16, a counter face 18, a seal 30, a vial cap 50, hole 52, a rebate 53 with a cylinder-shaped inner surface, location pins 60, a coil spring 70, a U shaped permanent clip 72 and an arrow A depicting the direction of force applied to cap 50.

FIG. 3 is a perspective view of an upper portion of vial 200 in a closed position. Vial body 10 has retention wings 14 on each side that permit vial 200 to interlock within a receiving cavity (not shown) within meter 1. U-shaped clip 72 straddles cap 50, resting on top of a coil spring 70 that is located within a cylinder-shaped rebate 53. Clip 72 interlocks with vial body 10 at rebates 12 which are located directly under the sealing counter face 18 of vial body 10. Clip 72 is made of steel or other suitably rigid material, and is permanently attached to vial 200 during manufacture thereof, and stays attached to vial 200 during use i.e. during opening and closing of vial cap 50 for dispensing of a test strip. In addition, offset holes 52

(and item 78 seen in FIG. 1) are located either side of cylinder-shaped rebate 53 and provide means to interlock vial cap 50 with lifting pegs 51 when vial 200 is inserted into meter 1. Gear train 46 operates lifting pegs 51 to lift vial cap 50 against the force of spring 70 to allow a test sensor to be delivered to the user.

A seal 30, optionally made from resiliently deformable material, such as Santoprene™ rubber for example, available from Advanced Elastomer Systems, Akron, Ohio, U.S.A. or alternative suitably resiliently deformable semi-impermeable material, may be two-shot moulded into and line the underside of vial cap 50. Seal 30 may optionally overlap the periphery of the rim of vial cap 50. Optionally, seal 30 deforms a predetermined amount when a known force is applied. The force applied to cap 50 against counter face 18 is generated by the action of U-shaped clip 72 straddling over coil spring 70 and vial cap 50, connecting at rebates 12, thereby providing a closure force when vial cap 50 is in the closed position i.e. when lifting pegs 51 are not operating to lift cap 50 away from vial body 10. In this closed position, spring 70 forces vial cap 50 to engage with vial body 10 in the direction indicated by arrow A, causing seal 30 to abut counter face 18 on vial body 10. Compression of seal 30 provides a substantially moisture semi-impermeable seal. The test sensors housed within vial 200 are susceptible to moisture degradation. The shape and nature of various embodiments of seal 30 will be described in more detail in some of the following paragraphs.

Furthermore, locating pins 60, formed on two diagonally opposite corners of vial cap 50, extend beyond the depth of cap 50. During the raising and lowering of cap 50 i.e. the opening and closing thereof, locating pins 60 guide the relative positions, and hence engagement thereof, of vial cap 50 and vial body 10. Locating pins 60 are provided to reduce the possibility of vial cap 50 becoming offset in relation to counter face 18 of vial body 10 during re-engagement. Misalignment of vial cap 50 and vial body 10 may allow transmission of moisture vapour into vial 200. Although this example embodiment utilizes locating pins, it would be apparent to a person skilled in the art that varying designs and sizes of pins, or other means to allow fixture of the vial cap 50 onto the counter-face (not shown) of vial 10 are possible.

Figure 4:
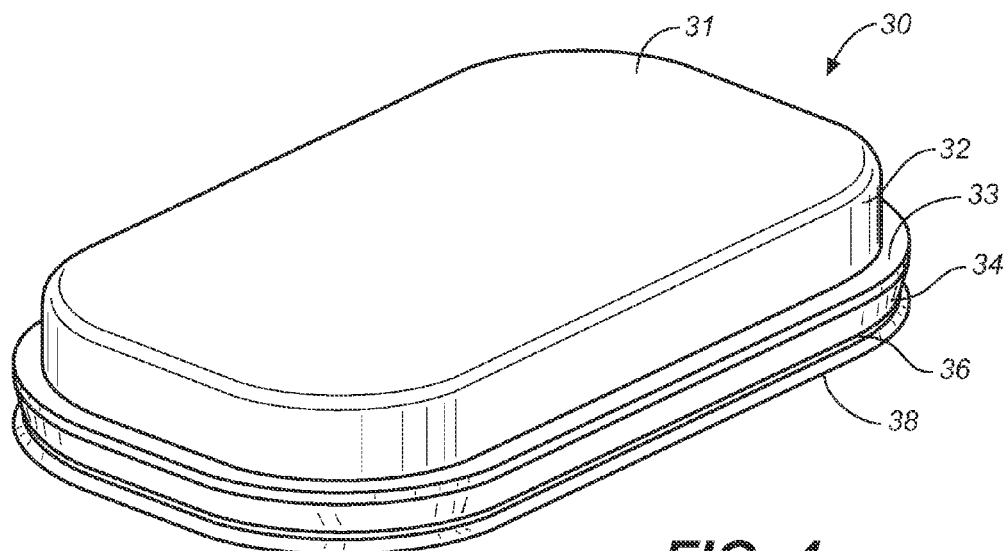
FIG. 4 shows a perspective view of a first example embodiment of a seal according to the invention.

FIG. 4 shows a perspective view of a first example embodiment of a seal 30 according to the invention, comprising a substantially planar upper wall 31, an annular mating face 32, an annular ledge 33, an annular flange 34, an annular line of weakness (which may also be referred to as a hinge) 36, and a skirt 38. In this particular example embodiment, seal 30 lines the entire inner structure of cap 50 (seen in FIG. 3). Alternatively, seal 30 may be annular in shape having no substantially planar upper wall 31. In this case, seal 30 may simply line an annular inner wall of cap 50. While only one annular line of weakness is mentioned, and at least one is preferred, a seal with none, or more than one line of weakness is also envisaged.

Figure 5:
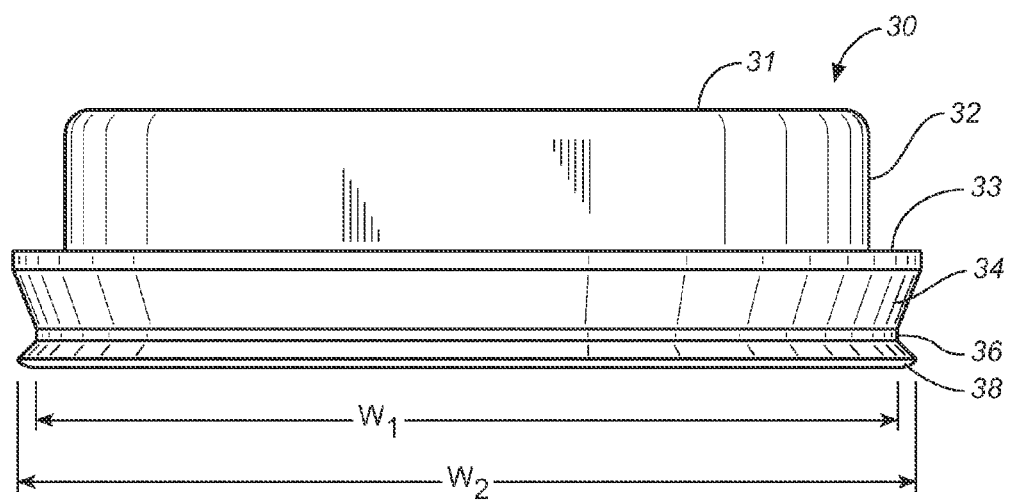
FIG. 5 shows a side elevation view of the seal of FIG. 4.

FIG. 5 shows a side elevation view of a seal 30 according to a first example embodiment of the invention, comprising a substantially planar upper wall 31, an annular mating face 32, an annular ledge 33, an annular flange 34, an annular line of weakness (which may also be referred to as a hinge) 36, and a skirt 38.

FIG. 4 show a perspective view of a first example embodiment of a seal 30 according to the invention, and FIG. 5 shows a side elevation view of the seal 30 of FIG. 4. Seen from a side elevation view, the profile of seal 30 is more clearly depicted.

In this example embodiment, seal 30 is substantially rectangular in shape with rounded corners, and may be made from a deformable material such as Santoprene™ available from Advanced Elastomer Systems, Akron, Ohio. Although this example embodiment utilizes a generally rectangular shaped rubber seal with rounded corners, it would be apparent to a person skilled in the art that varying shapes and sizes of seals, would be conceivable, such as circular, oval, triangular, square, octagonal and so on. It would also be apparent to someone skilled in the art that one or more other deformable materials could be used, or even a combination of rigid and deformable materials.

Seal 30 comprises a substantially planar upper wall 31 with a substantially perpendicular mating face or wall 32 depending from the entire periphery thereof. Mating face 32 may be in the range of 1 to 7 mm in height and preferably closer to 5 mm. A substantially flat annular ledge 33 is formed substantially perpendicular to annular mating face 32, in a radially outwards direction i.e. generally parallel to upper wall 31. Annular ledge 33 has a width in the range between 1 to 5 mm but preferably closer to 2 mm. Seal 30 has an annular flange 34 downwardly extending approximately 3 mm (when uncompressed) from the periphery of annular ledge 33, towards an annular line of weakness (which may also be referred to as a hinge) 36. In this embodiment, annular flange 34 has a chamfered, generally triangular cross-section, and is arranged to deform outwardly away from the center of cap 50 upon compression (as will be shown in FIGS. 5 to 7 and 12). Annular line of weakness (which may also be referred to as a hinge) 36 separates annular flange 34 from an annular skirt 38. Annular skirt 38 protrudes outwardly from deformable flange 34 and extends approximately 0.5 mm from line of weakness (which may also be referred to as a hinge) 36. In this embodiment, annular skirt has a generally rectangular cross-section and is arranged to deform outwardly away from the center of cap 50 upon compression (as will be shown in FIGS. 6, 7 and 12).

Figure 7:
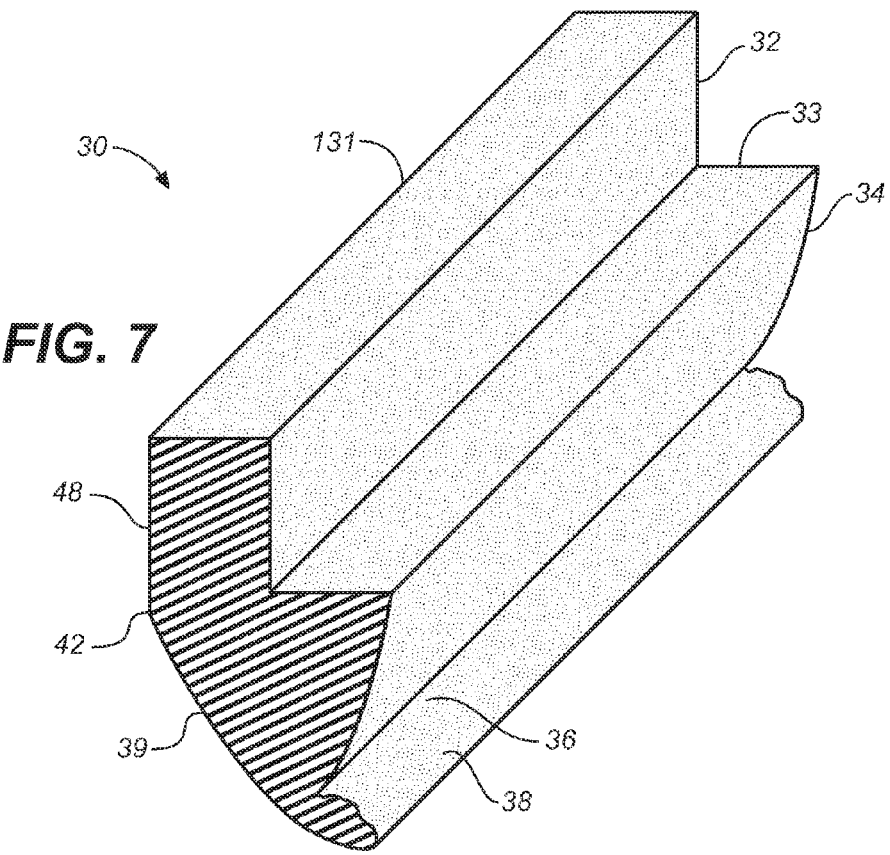
FIG. 7 shows a cross-sectional view of a finite element analysis model of the seal of FIG. 6 in its compressed state.

Skirt 38 abuts counter face 18 of vial body 10 when seal 30 is located on, and optionally embedded within vial cap 50, and is under the force of spring 70 as shown in FIG. 3. The chamfered, generally triangular cross-section of annular flange 34 (as shown in FIG. 7) means that flange 34 is relatively un-deformable, whereas the relatively thin cross-section of skirt 38 is relatively deformable. Optionally, annular skirt 38 is sized to have a slightly greater width $W_2$ than the comparable width $W_1$ of annular line of weakness (which may also be referred to as a hinge) 36, so that skirt 38 is compressed radially outwardly by flange 34. Additionally, the dimensions such as height and relatively flexible nature of skin 38 is such, as to allow a seal to be formed against non-flat surfaces or pitted surfaces in counter-face 18, that may result from the manufacturing process.

Optionally, seal 30, vial cap 50 and vial body 10 may be black in colour or any other colour, optionally a dark colour, sufficient to block light from falling onto test sensors held therein.

Figure 6:
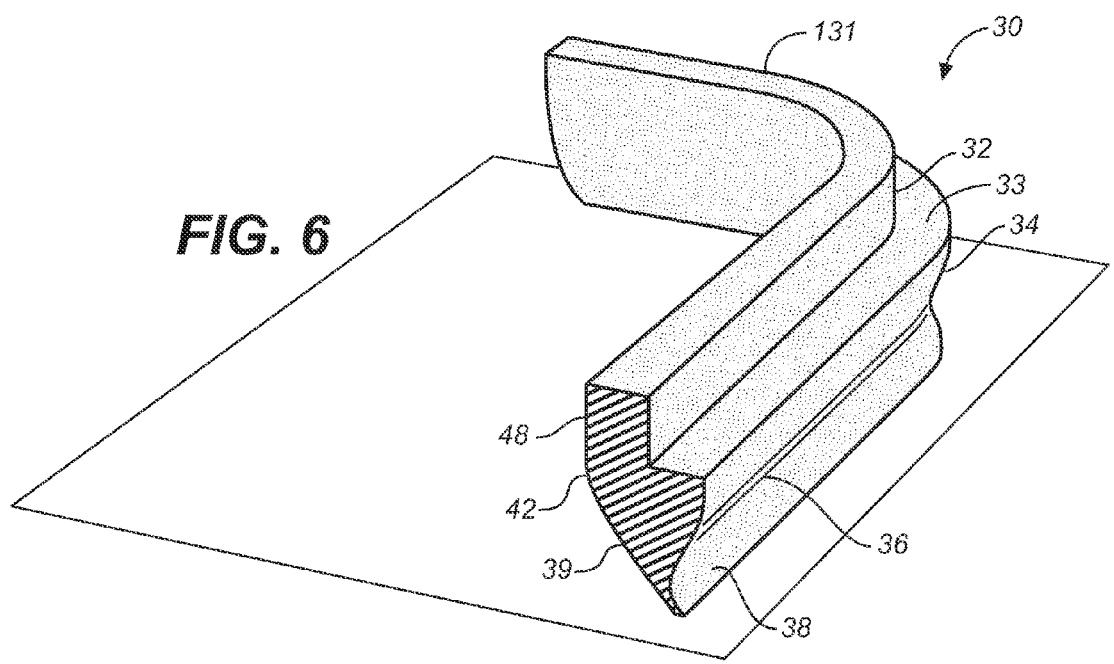
FIG. 6 shows a cross-sectional view of a finite element analysis model of an embodiment of the seal seen in FIGS. 4 and 5, in its uncompressed state.

FIG. 6 shows a cross-sectional perspective view of a finite element analysis model of seal 30 of FIGS. 4 and 5, comprising a flat upper surface 131, a mating face 32, an annular ledge 33, a flange 34, an annular line of weakness (which may also be referred to as a hinge) 36, a skirt 38, an inner angled wall 39, a point of inflection 42, and an innermost wall 48.

FIG. 6 shows a cross-section perspective view of seal 30 in its uncompressed state. Seal 30 is made from a deformable material, as previously described, such as Santoprene™ and available from Advanced Elastomer Systems, Akron, Ohio. A substantially flat upper surface 131 is formed with a substantially perpendicular mating face 32 depending from the outermost periphery thereof. In addition, an innermost wall 48 is formed depending from the innermost periphery of substantially flat upper surface 131. In this first embodiment, mating face 32 is in the range of 1 to 7 mm in height but preferably closer to 5 mm with an annular ledge 33 formed substantially perpendicular to mating face 32. Annular ledge 33 is a substantially planar surface with a width in the range between 3 to 5 mm but preferably closer to 2 mm. Seal 30 has an annular flange 34 depending from the periphery of annular ledge 33. Annular flange 34 is generally triangular in shape, and extends toward an annular line of weakness (which may also be referred to as a hinge) 36. Line of weakness (which may also be referred to as a hinge) 36 separates annular flange 34 from annular skirt 38. In this embodiment, annular skirt 38 is angled outwardly away from an inwardly angled outer wall of generally triangular shaped annular flange 34. Skirt 38 has a height of approximately 1 mm.

An inner outwardly angled wall 39 generally triangular shaped flange 34 extends between line of weakness (which may also be referred to as a hinge) 36 and a point of inflection 42. The point of inflection 42 is located at the point at which angled wall 39 and innermost wall 48 meet. The generally square shape (in this case triangular shape) of annular flange 34 ensures that annular flange 34 is relatively stiff, whereas in contrast skirt 38 is relatively flexible. Annular skirt 38 is compressed radially outwards towards flange 34 during abutment to counter face 18. Thus, skirt 38 abuts counter face 18 of vial body 10 when seal 30 is located on, or optionally embedded within vial cap 50, and is under the force of spring 70 (as shown in FIG. 3).

FIG. 7 shows a cross-sectional view of a finite element analysis model of a vial seal 30 in its compressed state according to an example embodiment of the invention, comprising a flat upper surface 131, a mating face 32, an annular ledge 33, an annular flange 34, a line of weakness (which may also be referred to as a hinge) 36, a skirt 38, an inner angled wall 39, a point of inflection 42, and an innermost wall 48.

FIG. 7 shows a cross-section perspective view of seal 30 in its compressed state i.e. showing the deformation which typically occurs when skirt 38 abuts counter face 18 under the closure force provided by the interaction of clip 72 and spring 70. FIG. 7 shows all the same features as previously described in relation to FIG. 6.

During abutment of seal 30 with counter face 18, inner angled wall 39 of flange 34 forms an arcuate shape. When seal 30 is compressed against counter face 18 of vial body 10, the greatest degree of deformation is experienced by skirt 38. Skirt 38 outwardly deforms in the direction whereby outermost surface of skirt 38 becomes substantially parallel to annular ledge 33. The greatest deformation occurs at the line of weakness (which may also be referred to as a hinge) 36. In addition, although to a lesser extent because of its relatively less deformable nature, annular flange 34 experiences some outwards deformation under the closure force of spring 70. The previously innermost surface of skirt 38 now presses against sealing counter-face 18 by the action of flange 34 upon it, thus ensuring a continuous seal on counter-face 18 of vial body 10. The relatively flexible nature of skirt 38 performs two functions. Firstly it provides a continuous seal around the opening in counter-face 18, and secondly it can fill any imperfections such as pits or channels on counter-face 18.

Figure 8:
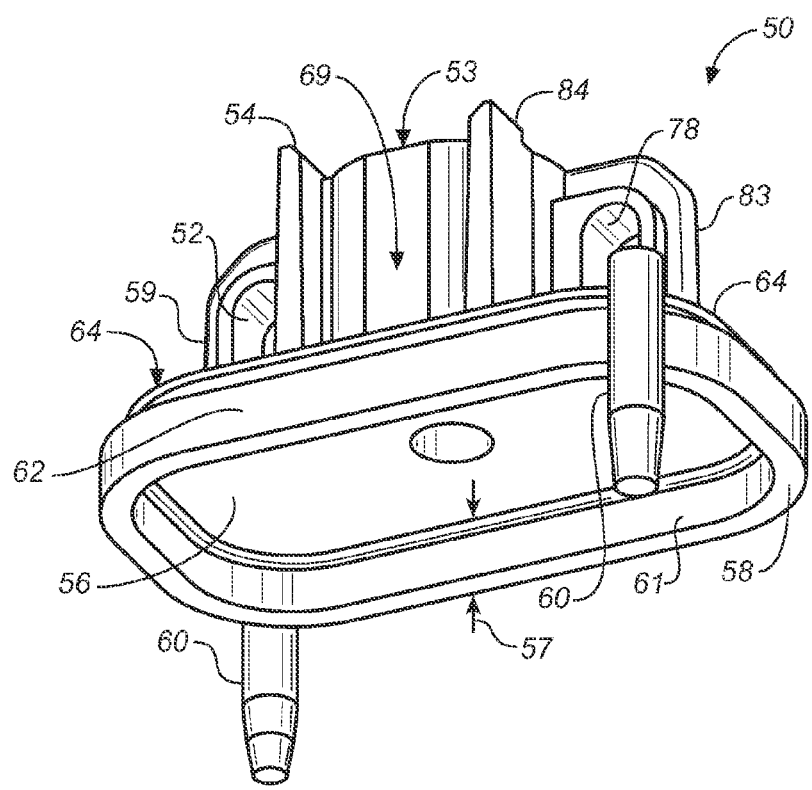
FIG. 8 shows a perspective view of a vial cap according to an example embodiment of the invention.

FIG. 8 shows a perspective view of an example embodiment of a vial cap 50 including offset holes 52 and 78, a rebate 53 with a cylinder-shaped inner surface, a gap or groove 69, faces 54 and 84, an inner cap mating face 56, a well depth 57, a cap-rim 58, wings 59 and 83, locating pins 60, an innermost wall 61, vial cap outer face 62, and an outermost surface 64. Vial cap 50 may be manufactured from glass filled polypropylene or other suitable rigid material.

Figure 9:
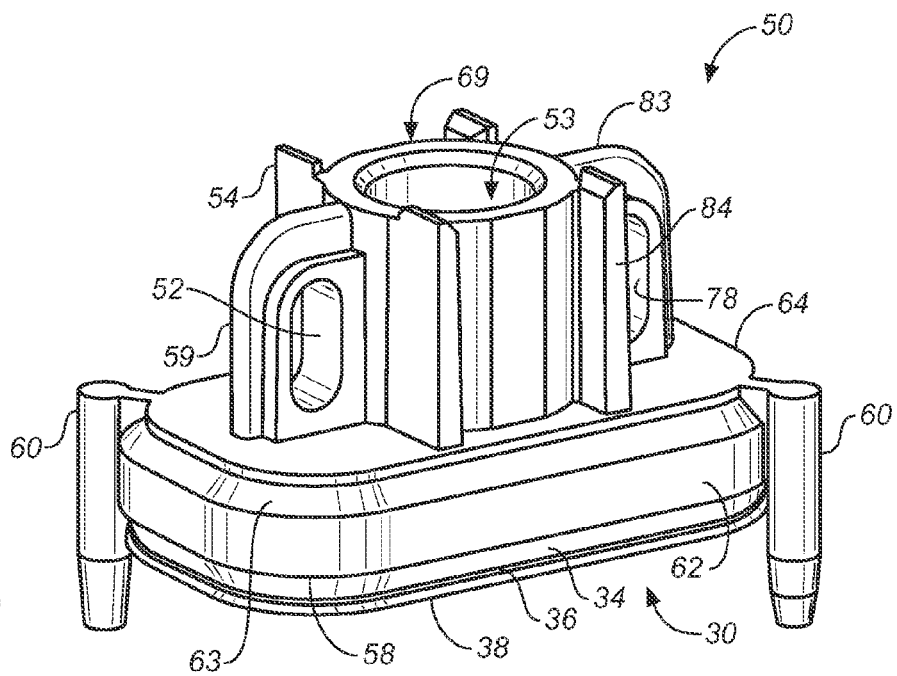
FIG. 9 shows a perspective view of the vial cap of FIG. 6, lined with the seal of FIGS. 4 and 5, according to an example embodiment of the invention.

FIG. 9 shows a perspective view of a vial cap 50 and seal 30 according to an embodiment of the invention comprising a flange 34, a line of weakness (which may also be referred to as a hinge) 36, an annular skirt 38, a first hole 52, a second hole 78, a rebate 53 with a cylinder-shaped inner surface for receiving a spring 70, a first face 54, a cap rim 58, a second face 84, a first wing 59, a second wing 83, a locating pins 60, an annular outermost wall 62, a chamfered profile 63, and an outermost surface 64. FIG. 9 shows a perspective view of a vial cap 50 and 30 that by way of example, may be two-shot moulded therein. Alternative techniques can be used to attach seal 30, for example sticking, embedding or welding within vial cap 50, such as those known to persons skilled in the art.

Referring now to FIGS. 8 and 9, vial cap 50 includes a rebate 53 with a cylinder-shaped inner surface for receiving spring 70 (as seen in FIG. 3), centrally moulded on outermost surface 64. Rebate 53 has an open end substantially parallel to outermost surface 64 of cap 50, and a second end (not shown) directly opposite the first end. Second end of spring holding cylinder 53 substantially abuts outermost surface 64 thus forming a one-ended cylinder. Two faces 54 and 84 are located substantially perpendicular to outermost surface 64 of vial cap 50, and form part of the external walls of rebate 53. Faces 54 and 84 are substantially parallel to one-another, and extend beyond the diameter of rebate 53 thereby forming a gap or groove 69 there-between that allows a U-shaped clip 72 to straddle over vial cap 50 as shown in FIGS. 1 to 3. Wings 59 and 83 are formed substantially perpendicular to faces 54 and 84 respectively, and substantially perpendicular to outermost surface 64 of vial cap 50. Wings 59 and 83 are centrally formed on outermost surface 64 of cap 50, and are located on two opposing sides of rebate 53. Furthermore, wings 59 and 83 include holes 52 and 78 respectively (that may or may not be offset with respect to each other). Holes 52, 78 and/or retention wings 14 (on vial body 10) may be offset with the purpose of allowing the vial 200 to be inserted into a cavity of meter 1 in one orientation only. Holes 52 and 78 cooperate with arms 51 of a lifting mechanism of meter 1 (shown in FIG. 2).

Two locating pins 60 are located on diagonally opposing corners of vial cap 50 and protrude between approximately 3 and 7 mm (preferably about 5 mm) beyond cap rim 58. Locating pins 60 are formed on diagonally opposing corners of outermost surface 64 of vial cap 50 to increase the efficiency of the upward and downward movement of vial cap 50 i.e. opening and closing thereof, when it is inserted in a cavity (not shown) within meter 1. Optionally, locating pins 60 help to ensure seal 30 is correctly located with respect to countersurface 18 of vial body 10 (as shown in FIG. 3) i.e. vial cap 50 does not become offset with relation to vial counter-face 18 for whatever reason. Such an offset of vial cap 50 from counter-face 18 may cause the seal to fail or perform incorrectly and may allow the ingress of moisture into vial body 10 causing degradation to the accuracy of the test sensors housed within.

FIG. 8 shows an inner seal mating face 56, generally rectangular in shape and surrounded by a substantially perpendicular inner wall 61. The depth of wall 61 is typically between 1 and 3 mm (preferably about 2.8 mm), and inner wall 61 and mating face 56 together form a well 57 for allowing seal 30 to be embedded therein (shown in FIG. 9). Wall 61 has an annular cap-rim 58, formed substantially perpendicular to wall 61, of width between approximately 1 and 3 mm, and may be closer to 1.4 mm. In addition, cap-rim 58 has a substantially planar surface, in a plane substantially parallel to seal mating face 56.

Annular ledge 33 abuts against annular cap rim 58 of vial cap 50 (shown in FIG. 8) when seal 30 and vial cap 50 are interconnected (as shown in FIG. 9). Outwardly extending chamfered profile 63 is formed between outermost surface 64 of vial cap 50 and annular outermost wall 62, and extends in the direction away from outermost surface 64. Annular outermost wall 62 is substantially perpendicular to outermost surface 64, and has a depth of approximately 4 mm. Optionally, at least one line of weakness (which may also be referred to as a hinge) 36 separates annular flange 34 and annular skirt 38. Annular skirt 38 forms a semi-impermeable seal between vial cap 50 and counter face 18 of vial body 10 as shown in FIG. 3. Abutment between seal 30 and counter face 18 substantially excludes the intrusion of moisture to levels described in FIGS. 13 and 15.

Figure 10:
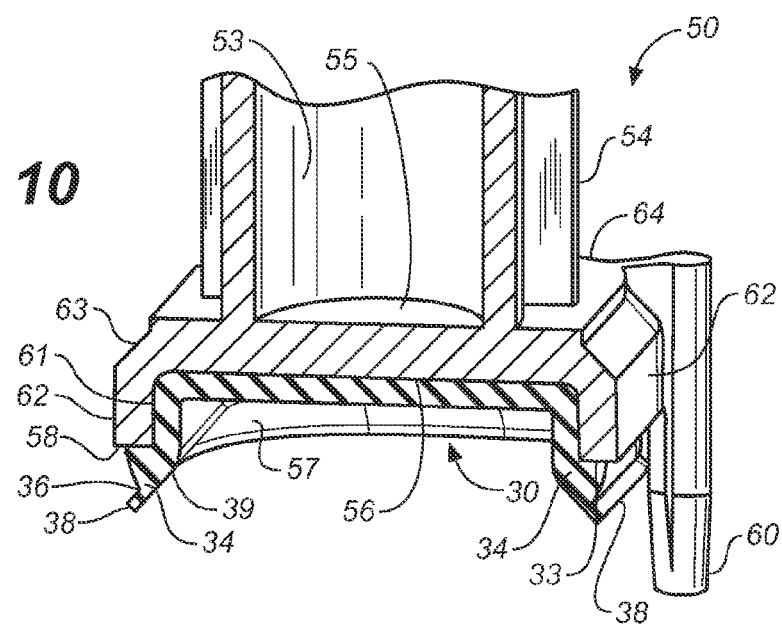
FIG. 10 shows a perspective, cross-sectional view of the vial cap and seal of FIG. 7.

FIG. 10 shows a perspective cross-sectional view of the vial cap 50 and seal 30 of FIG. 9, comprising an annular ledge 33, a flange 34, a line of weakness (which may also be referred to as a hinge) 36, an annular skirt 38, a spring holding cylinder 53, a face 54, a cylinder platform 55, a well 57, a cap-rim 58, a locating pin 60, an innermost wall 61, an outermost wall 62, a chamfered profile 63, and an outermost surface 64.

FIG. 10 shows a perspective, cross-sectional view of the vial cap 50 and seal 30 of FIG. 9. Rebate 53 for receiving spring 70 is formed substantially perpendicular to outermost surface 64 of vial cap 50, and is approximately 10 mm in length. As previously discussed, rebate 53 has at least one face 54 which is formed substantially perpendicular to outermost surface 64 and formed as part of the wall of rebate 53. Rebate 53 is designed specifically to house spring 70, ensuring spring 70 is substantially centrally located on outermost surface 64 of vial cap 50, and thereby distributes the closure force substantially evenly between vial cap 50 and vial body 10.

Rebate 53 and well 57 on the underside of vial cap 50 for receiving seal 30 are separated by a cap thickness in the range of 1 to 3 mm, but preferably of thickness 2.5 mm. Annular outermost wall 62 of vial cap 50 provides recessed well 57 therein for allowing fitment of seal 30 against mating face 56 and innermost wall 61. Walls 61 of well 57 are formed to be substantially perpendicular to planar surface 56 of well 57. Furthermore, upper mating face 31 of seal 30 mates with planar mating face 56 of recessed well 57. In addition, mating face 32 of seal 30 mates with innermost wall 61 of vial cap 50, and annular ledge 33 of seal 30 mates with cap-rim 58, forming an embedded seal 30 within recessed well 57. Although in this embodiment a two-shot moulding technique is used to form seal 30 within well 57, other techniques can be used as those known to persons skilled in the art. Such manufacturing techniques can, for example be the formation of a seal in isolation to the manufacturing of vial cap 50 with the seal then inserted and optionally glued or otherwise attached within recessed well 57. An annular seal with no upper wall 31 is also envisaged.

FIG. 10 shows annular ledge 33 of seal 30 partially covering cap-rim 58 i.e. rim 58 is wider than the width of annular ledge 33, thus providing an overhang. When seal 30 abuts counter face 18 of vial 10 under the force (approximately 7N) of coil spring 70, annular flange 34 may deform outwardly, in a direction towards cap-rim 58. Annular skirt 38 is designed specifically to deform upwardly towards cap-rim 58 under the closure force of spring 70. Additionally, inner angled wall 39 of annular flange 34 of seal 30 pushes annular skirt 38 outwardly when vial body 10 and vial cap 50 abut one another under the closure force of spring 70.

Figure 11:
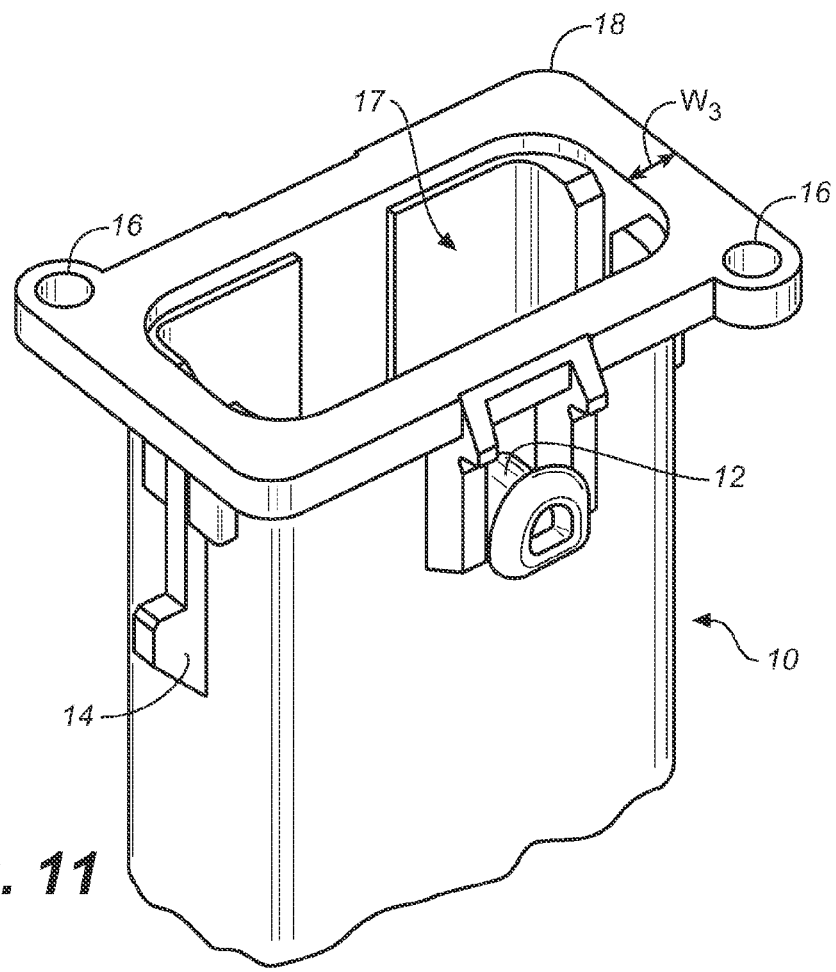
FIG. 11 shows a perspective view from above of a vial sealing counter face according to an example embodiment of the invention.

FIG. 11 shows a perspective view of an upper aspect of a vial sealing counter face 18 according to an embodiment of the invention, including a vial body 10 with an open end 17, a rebate 12, a retention wing 14, apertures 16 and a sealing counter face 18.

FIG. 11 shows a perspective view of an upper aspect of a vial sealing counter face 18 according to an embodiment of the invention. Vial body 10 is formed from an injection molding process forming a substantially rectangular shaped container. A first end of vial body 10 is sealed (not shown) and the opposite end thereof is open 17. The substantially rectangular shaped vial 10 is formed to accommodate test sensors (as depicted in FIG. 1).

Open end 17 of vial body 10 is substantially rectangular in shape and has an annular sealing counter face 18. Counter face 18 is formed on the rim of the walls of vial body 10, and has a width greater than the width of the walls of vial body 10 thereby creating an outwardly extending overhang around the periphery. Width $W_3$ of counter face 18 is in the range of 5 to 7 mm, but preferably 6.4 mm. Counter face 18 of vial body 10 has a substantially planar surface typically produced during the manufacturing process thereof, although it is envisaged that less-planar surfaces are also possible during such a manufacturing process. The tight abutment between seal 30 and counter face 18 is for mitigating the negative effect of moisture on test sensors held within vial body 10. Although counter face 18 is hereby shown to have a substantially planar surface, seal 30 of vial cap 50 may provide the same sealing properties if surface of counter face 18 is uneven i.e. has pits or channels formed during manufacture thereof.

It is also envisaged that the sealing counter-face may be provided on cap 50, and an annular seal on a vial body 10, according to a further example embodiment of the invention.

Two apertures 16 for receiving location pins 60 are formed on diagonally opposed corners of counter face 18. Although two apertures 16 are shown in this example embodiment on diagonally opposing corners of counter face 18, it would be apparent to a person skilled in the art that varying locations, shapes, size and/or number of apertures are conceivable and is not restricted. For example, one or more locating pins 60 may be on the vial body 10 to cooperate with one or more apertures on cap 50 and/or vice versa. Apertures 16 cooperate with locating pins 60 during the opening and closing of vial 200 to dispense a test sensor to a user.

Rebates 12 are formed on two directly opposite faces of vial body 10. Retention wings 14 are formed on the remaining two faces of vial body 10, and may be positioned at a distance slightly further from counter face 18. U-shaped clip 72 (shown in FIGS. 1 to 3) straddles vial cap 50 and interlocks with rebates 12 of vial body 10. A coil spring 70 is interlocked within U-shaped clip 72 and is compressed within rebate 53 thus providing equal pressure to seal 30 on counter face 18 during abutment thereof. Vial cap 50 is guided into its open and closed position by interaction of locating pins 60 and apertures 16. The open and closed position of vial cap 50 is conducted by the action of gearing mechanism 46 to dispense a test sensor to the user, as described previously.

Vial 10 and vial cap 50 are manufactured from polypropylene and available from Borealis, Denmark and can be used in a process called injection moulding. Typically, materials such as polypropylene are thermoplastics, which allow them to be pressured in a mould when they are heated, to form different shapes.

The example embodiments of a vial cap 50 and vial body 10 described herein may be black in colour, although any colour of any suitable material e.g. plastic such as thermoplastic may be used.

Figure 12:
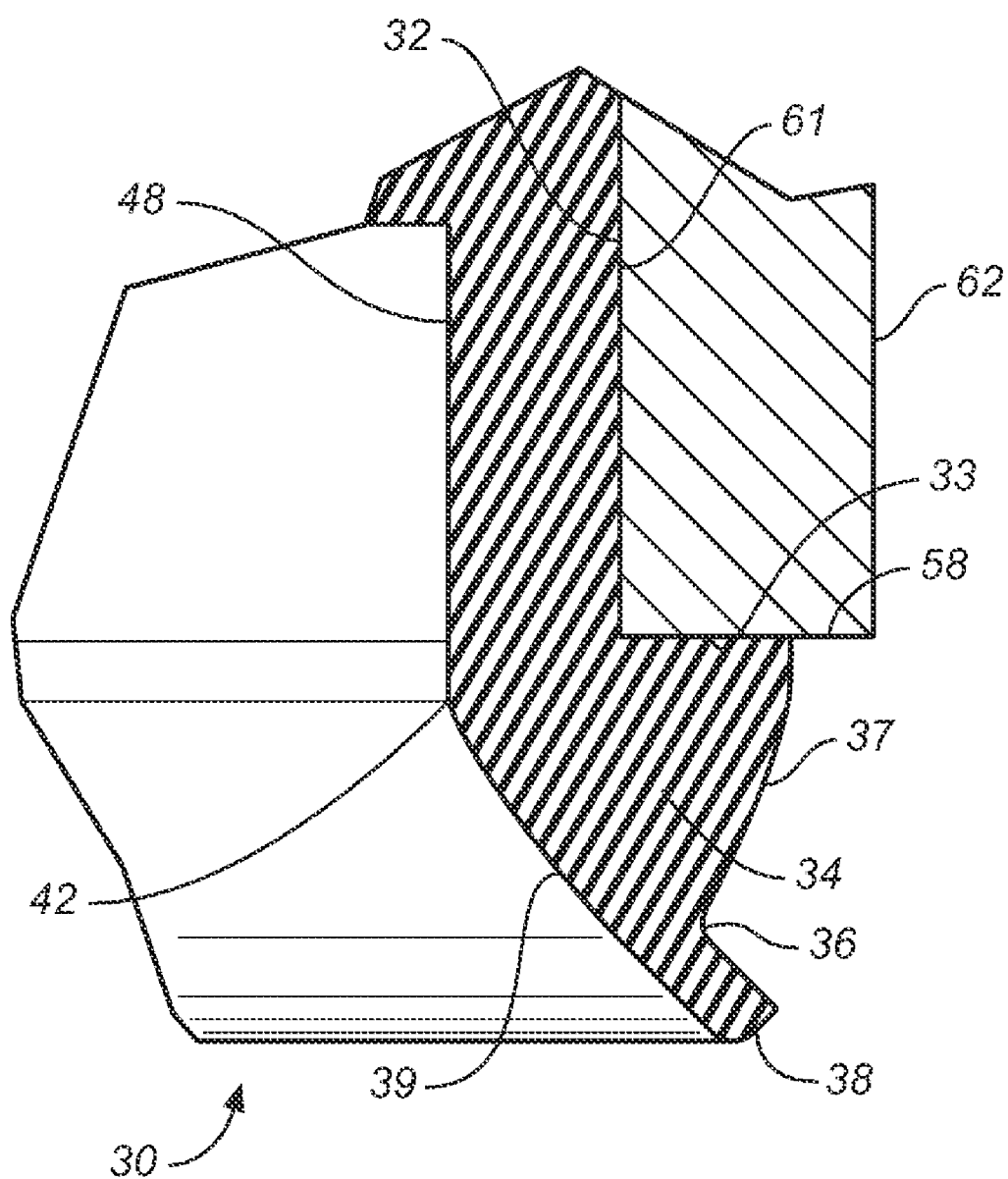
FIG. 12 shows a cross-sectional view of the seal of FIGS. 4 to 7 and 9 to 10.

FIG. 12 shows a cross-sectional view of a vial seal 30 according to an embodiment of the invention, comprising a mating face 32, an annular ledge 33, a flange 34, an annular line of weakness (which may also be referred to as a hinge) 36, an outer angled wall 37, a skirt 38, an inner angled wall 39, a point of inflection 42, an innermost wall 48, a cap rim 58, a cap innermost surface 61 and a cap outermost surface 62.

FIG. 12 shows a cross-section of a seal 30 according to an embodiment of the invention, as described previously in relation to FIGS. 4 to 7 and 9 to 10. Vial cap 50 comprises an innermost surface 61, an outermost surface 62 and a cap rim 58. Cap outermost surface 62 is substantially perpendicular to cap rim 58 and is substantially parallel to inner wall 61 of cap 50. Seal 30 has a seal mating face 32 that abuts inner wall 61 of vial cap 50. Seal mating face 32 may be fixedly attached to inner wall 61 of vial cap 50 through a two-shot moulding process, or alternatively seal mating face 32 may be glued or otherwise affixed against inner wall 61.

Innermost wall 48 and mating face 32 of seal 30 are typically substantially parallel to one another. In addition, innermost wall 48 and mating face 32 are approximately 4 mm in length. Annular ledge 33 is substantially perpendicular to mating face 32 and abuts annular cap rim 58 of vial cap 50. Optionally, annular cap rim 58 is substantially wider than annular ledge 33 of seal 30 thereby forming an overhang. The overhang of annular cap rim 58 beyond annular ledge 33 is approximately 3 mm in length.

Seal 30 of FIG. 12 has two arcuate profiles, an outer angled wall 37 and an inner angled wall 39. Both walls 37 and 39 are slightly arcuate in a convex manner and are separated from skirt 38 by annular line of weakness (which may also be referred to as a hinge) 36. Outer angled wall 37 extends inwardly from cap rim 58, whereas inner angled wall 39 extends outwardly from cap rim 58. Walls 37 and 39 extending towards each other to form generally triangular shaped flange 34.

During use, skirt 38 abuts counter face 18 of vial body 10 and deforms outwards and towards cap rim 58 thus forming a tight seal between cap 50 and counter face 18 to reduce the possibility of moisture ingress into the vial.

Figure 13:
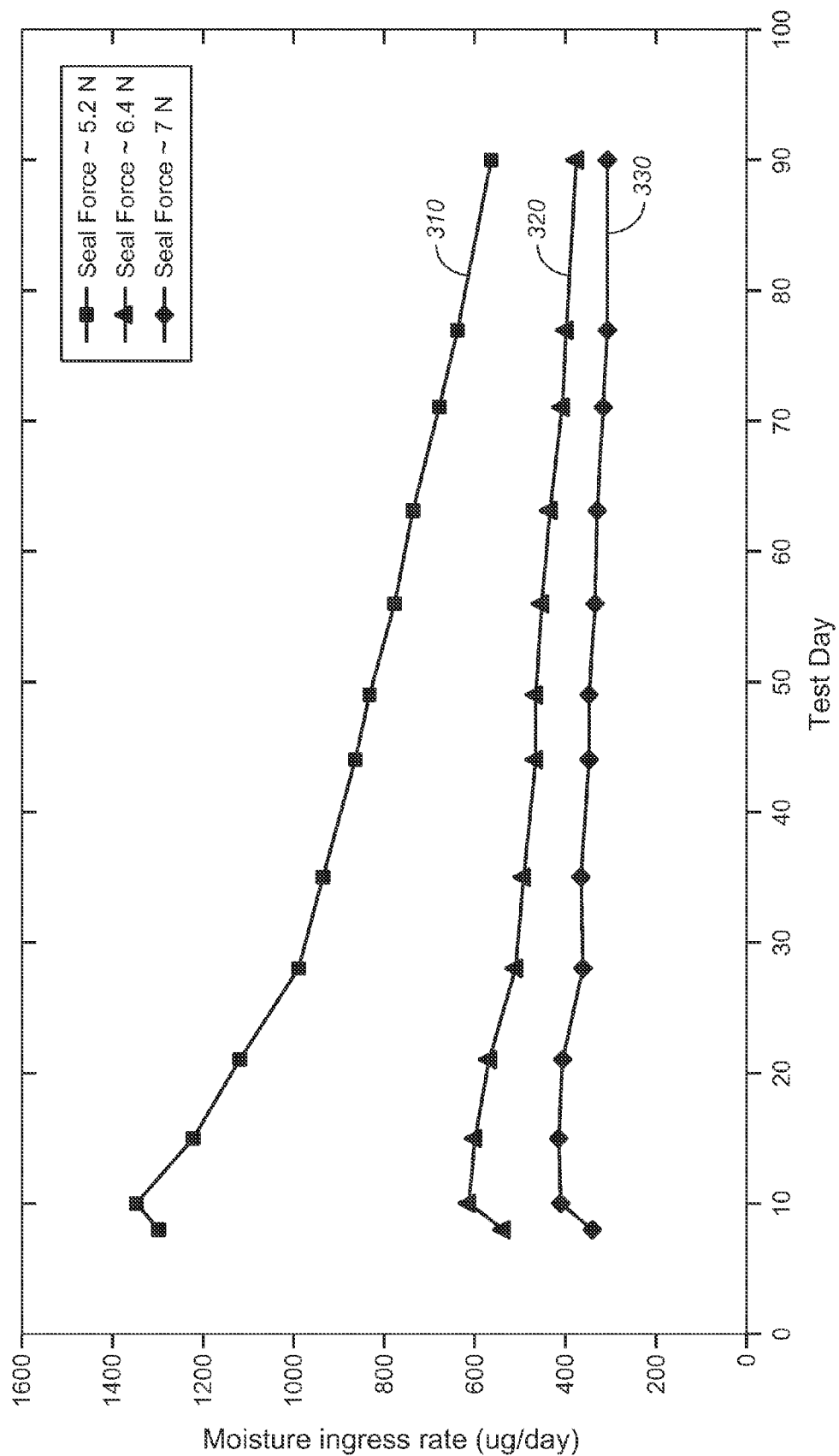
FIG. 13 shows three plots of moisture ingress with time for the first embodiment of a seal (of FIGS. 4 to 7 and 9 to 10) with closure forces of 5.2 N, 6.4 N and 7 N applied.

FIG. 13 shows three plots of moisture ingress with time for the first embodiment of a seal 30 (of FIGS. 4 to 7, 10 and 12), including a first line 310 depicting the results obtained for a first vial closure force (~5.2N), a second line 320 depicting the results obtained for a second closure force (~6.4N) and a third line 330 depicting the results obtained for a third closure force (~7N).

Rates of moisture ingress may be determined by measuring the increase in weight over time. Seal 30 may be used with a vial containing desiccant (such as the vial 200 of FIG. 1) to protect test sensors from ambient conditions. The total weight of the vial 200 may be determined on day 0, and each subsequent day thereafter. The rate of moisture ingress can then be determined by dividing the increase in weight by the test day. Fluctuations in the initial results obtained are typically observed while the vials and desiccant acclimatise to the measurement conditions. Typically the rates of moisture ingress stabilise after approximately 7 days.

In FIG. 13, three different representation of moisture ingress are depicted, under increasing sealing forces, approximately 5.2 N, approximately 6.4N and approximately 7N. The rate of moisture ingress into vial 200 was measured over time to determine the shelf life of the test sensors housed within. Results of the least force (line 310) show the most moisture ingress having a peak of 1400 ug/day and reducing to 600 ug/day over a period of 80 days. Although, a downward trend is depicted, a substantial amount of moisture ingress would penetrate into vial 200, potentially causing deterioration in the test sensors. Line 320 depicts the rate of moisture ingress against time for a closure force of approximately 6.4 N, with a peak of 600 ug/day, reducing to 450 ug/day after 90 days. The increase in closure force from 5.2 N to 6.4 N gave a decrease in the rate of moisture ingress into vial 200, and the resulting rate of moisture ingress will have a lesser detrimental effect on the test sensors over the expected lifetime (approximately 18 months if the packaging is un-opened, or approximately 90 days once in use). A closure force of approximately 7N depicted by line 330 shows a constant moisture ingress rate of approximately 400 ug/day over the 90-day test. To achieve the target shelf life of the test sensors, a moisture ingress rate of less than 450 ug/day was achieved using a closure force of approximately 7N. This low rate of moisture ingress is deemed acceptable for the number of test sensors held within vial 200, and the relative constancy allows a longer shelf life to be ascertained compared to other sealing forces.

Figure 14:
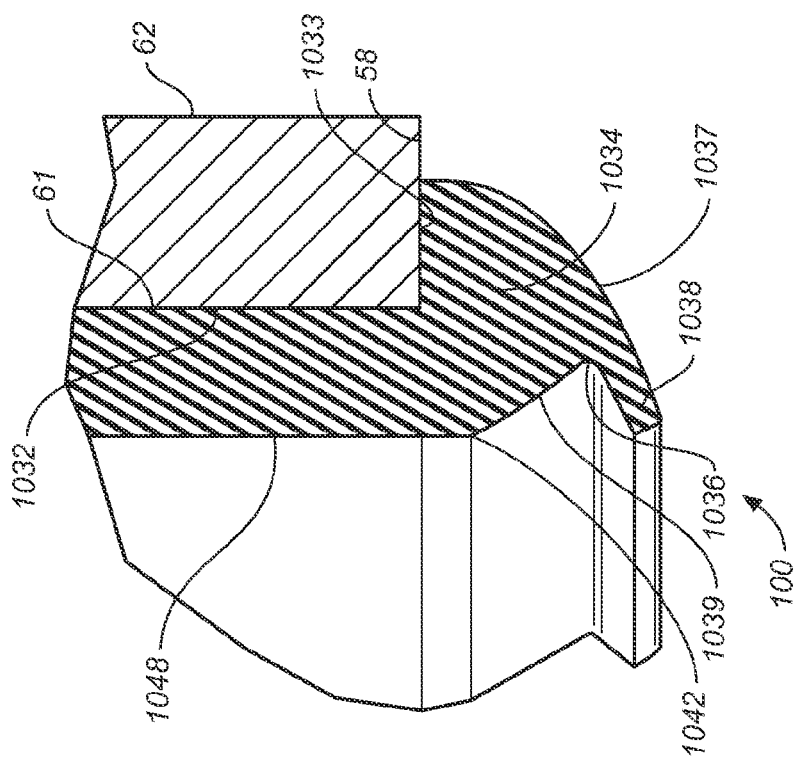
FIG. 14 shows another example embodiment of a seal according to the invention.

FIG. 14 is a cross-sectional view of a seal 100 according to yet another embodiment of the invention, comprising a cap rim 58, a cap inner surface 61, a cap outermost surface 62, a mating face 1032, an annular ledge 1033, an annular flange 1034, an inwardly chamfered outer wall 1037, a skirt 1038, an annular line of weakness 1036, an outwardly chamfered inner wall 1039, a point of inflection 1042 and an innermost wall 1048.

Figure 15:
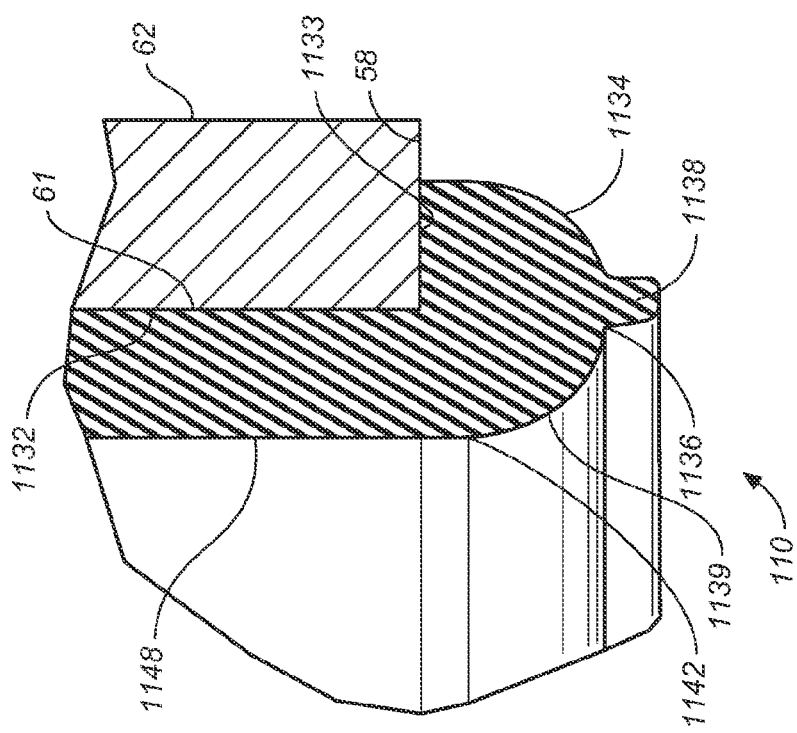
FIG. 15 shows another example embodiment of a seal according to the invention.

FIG. 15 is a cross-sectional view of a seal 110 according to yet another embodiment of the invention, comprising a cap rim 58, a cap inner surface 61, a cap outermost surface 62, a mating face 1132, an annular ledge 1133, an annular flange 1134, an inwardly chamfered outer wall 1137, a skirt 1138, an annular line of weakness 1136, an outwardly chamfered inner wall 1139, a point of inflection 1142 and an innermost wall 1148.

Figure 16:
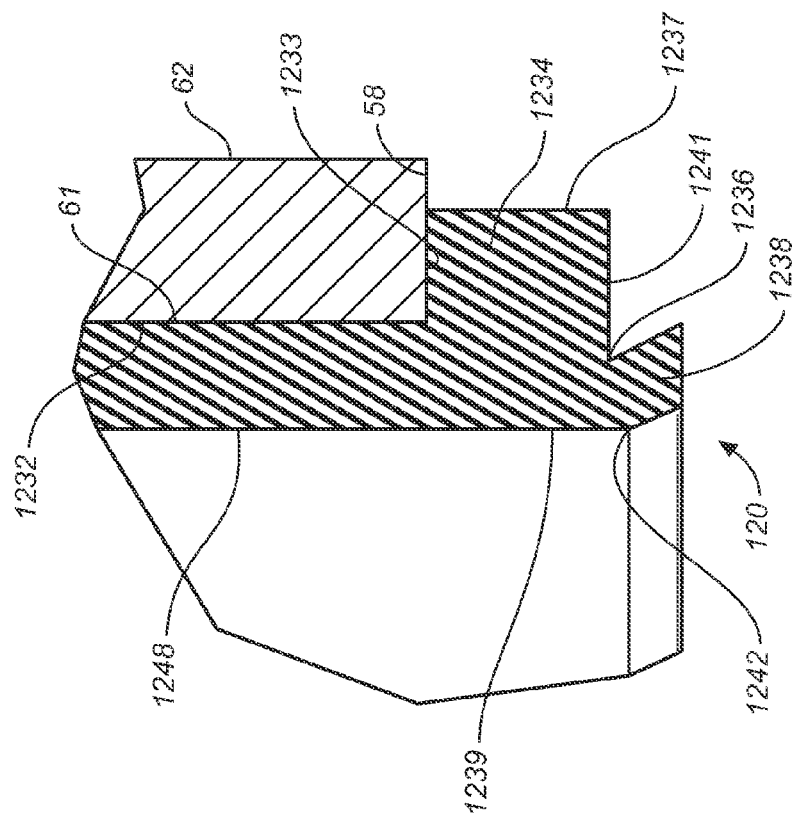
FIG. 16 shows another example embodiment of a seal according to the invention.

FIG. 16 is a cross-sectional view of a seal 120 according to yet another embodiment of the invention, comprising a cap rim 58, a cap inner surface 61, a cap outermost surface 62, a mating face 1232, an annular ledge 1233, a flange upper surface 1241, an annular generally square or rectangular flange 1234, an upwardly extending outer wall 1237, a skirt 1238, an annular line of weakness 1236, an innermost wall 1248, an upwardly extending inner wall 1219 and a line of inflection 1242.

Figure 17:
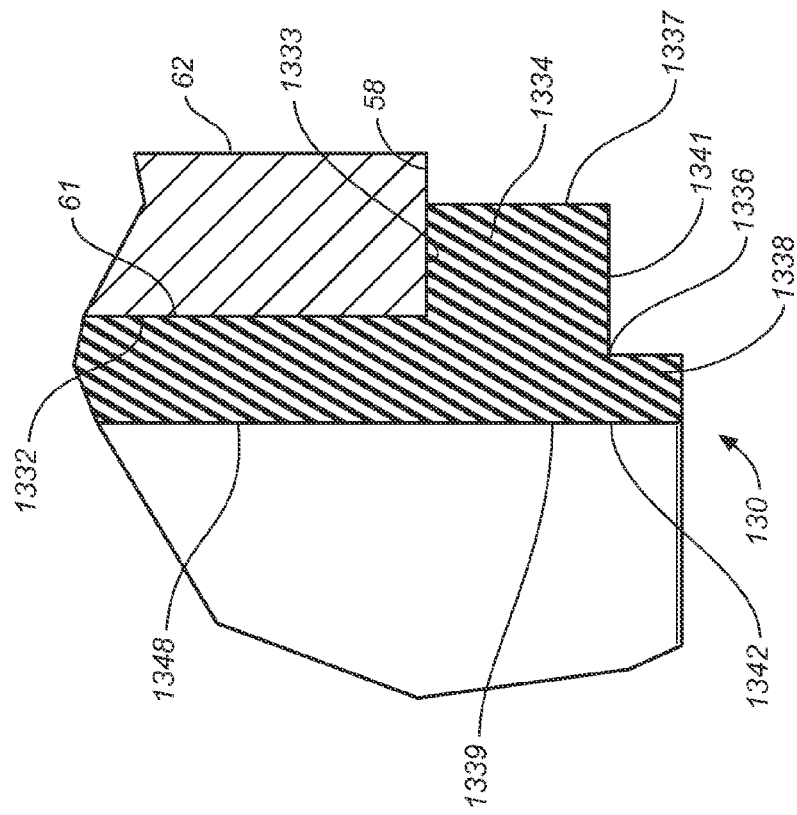
FIG. 17 shows another example embodiment of a seal according to the invention.

FIG. 17 is a cross-sectional view of a seal 130 according to yet another embodiment of the invention, comprising a cap rim 58, a cap inner surface 61, a cap outermost surface 62, a mating face 1332, an annular ledge 1333, a flange upper surface 1341, a generally square annular flange 1334, a generally square or rectangular skirt 1338, an annular line of weakness 1336, an upwardly extending outer wall 1337, an upwardly extending inner wall 1339 and an innermost wall 1348.

Further example embodiments of a seal according to the present invention are provided in FIGS. 14 to 17. The similarities and differences will now be discussed in turn. It can be noted that each example embodiment of a seal includes an innermost wall (items 1048, 1148, 1248 and 1138), a mating face (items 1032, 1132, 1232 and 1332) that is affixed to the inner surface 61 of the vial cap 50, and an annular ledge (items 1033, 1133, 1233 and 1333) that overlaps with and affixes to cap rim 58 by a suitable method such as two-shot moulding for example.

There is some general consistency in the shape of each of the example embodiments provided of a seal designed to mate with counter face 18 on vial body 10 to achieve a moisture semi-impermeable seal. Each example embodiment includes a wide base portion i.e. the portion of the seal that mates with cap rim 58. This base region is typically in the order of 2 to 4 mm wide, and in most of the example embodiments provided, this wide portion tapers towards a thin skirt portion that makes direct contact with counter face 18. Optionally, a seal may be affixed to the vial body 10, with a counter sealing-surface located on the vial cap 50.

This tapering may be in the form of annular concave surfaces, both internal and external, such as the example embodiment shown in FIG. 16. The tapering may optionally be achieved by inwardly or outwardly chamfered profiles, such as the examples shown in FIGS. 14 and 15. FIGS. 16 and 17 show examples whereby the wide portion extends in a columnar fashion, out of which directly protrudes the thinner skirt portion, with a line of weakness (items 1236 and 1336) formed therebetween.

FIG. 14 shows a skirt portion 1038 similar to the first embodiment of a seal 30 described previously in relation to FIGS. 4 to 7, 9, 10 and 12, although in this alternative embodiment skirt 1038 is formed protruding inwards towards the centre of vial cap 50. FIG. 15 shows a rounded or optionally square-shaped skirt portion 1138 protruding from the wider portion below, which chamfers equally on each side towards the base of skirt 1138. It would be obvious to a person skilled in the art that many different sizes and shapes of seal can be envisaged, and is not restricted to those described herein.

Where a skirt 38, 1038, 1138, 1238 and 1338 is provided, this may be integral with or separate but attached to flange 34, 1034, 1134, 1234, or 1334 respectively. Alternatively or in addition, indeed skirt 38, 1038, 1138, 1238 and 1338 may be made of the same or more flexible material than flange 34, 1034, 1134, 1234 and 1334.

What we claim is:

1. A vial including a stack of test sensors, said vial comprising a vial body and a vial cap, said vial including a seal, wherein said seal comprises:
    a vertical annular mating face;
    an annular ledge substantially perpendicular to the annular mating face;
    an annular flange attached to said annular ledge;
    an annular line of weakness, and a skirt wherein said annular line of weakness is positioned between said skirt and said flange such that said skirt is deformed and folds outward and the annular line of weakness deforms to a greater extent than the skirt when pressure is applied to said annular ledge and said skirt is pressed against a sealing surface of said vial body.

2. A vial including a stack of test sensors, said vial comprising a vial body and a vial cap, said vial including a seal, wherein said seal comprises:
    a substantially planar upper wall;
    an annular mating face;
    an annular ledge connected to said annular mating face and substantially perpendicular thereto;
    an annular flange connected to said annular ledge;
    an annular hinge; and
    a skirt
    wherein said annular hinge is positioned between said annular flange and said skirt such that said skirt folds outward when pressure is applied to said skirt.

3. A vial including a stack of test sensors, said vial comprising a vial body and a vial cap, said vial including a seal, wherein said seal comprises:
    a vertical annular mating face;
    an annular ledge substantially perpendicular to the annular mating face;
    a annular flange attached to said annular ledge and extending downwardly therefrom;
    an annular line of weakness and a skirt, wherein said annular line of weakness is positioned between said skirt and said flange such that said skirt is deformed and folds outward and the annular line of weakness deforms to a greater extent than the skirt when pressure is applied to said annular ledge and said skirt is pressed against a sealing surface of said vial body.

4. A vial including a stack of test sensors, said vial comprising a vial body and a vial cap, said vial including a seal, wherein said seal comprises:
    a substantially planar upper wall;
    an annular mating face extending downwardly from said upper wall;
    an annular ledge connected to said annular mating face and extending substantially perpendicularly from the annular mating face;
    an annular flange connected to said annular ledge and extending downwardly therefrom;
    an annular hinge; and
    a skirt
    wherein said annular hinge is positioned between said annular flange and said skirt such that said skirt folds outward when pressure is applied to said skirt.

* * * * *

UNITED STATES PATENT AND TRADEMARK OFFICE
CERTIFICATE OF CORRECTION

| | | |
|---|---|---|
| PATENT NO. | : 7,712,610 B2 | |
| APPLICATION NO. | : 11/553257 | |
| DATED | : May 11, 2010 | |
| INVENTOR(S) | : Bryan Tissington | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 843 days.

Signed and Sealed this
Eleventh Day of January, 2011

David J. Kappos
*Director of the United States Patent and Trademark Office*